US011236287B2

(12) United States Patent
Baldovini et al.

(10) Patent No.: US 11,236,287 B2
(45) Date of Patent: Feb. 1, 2022

(54) 2-OCTYLCYCLOPROPYL-1-CARBOXYLIC ACID AND THE ISOMERS THEREOF, AND USES OF SAME

(71) Applicants: Albert Vieille, Vallauris (FR); CENTRE NATIONAL DE LA RECHERCHE SCIENTIFIQUE (CNRS), Paris (FR); Universite De Nice, Nice (FR)

(72) Inventors: Nicolas Baldovini, Nice (FR); Céline Cerutti-Delasalle, Grasse (FR)

(73) Assignees: Albert Vielle, Vallauns (FR); Centre National de la Recherche Scientifique (CNRS), Paris (FR); Universite de Nice, Nice (FR)

( * ) Notice: Subject to any disclaimer, the term of this patent is extended or adjusted under 35 U.S.C. 154(b) by 0 days.

(21) Appl. No.: 15/528,225

(22) PCT Filed: Nov. 18, 2015

(86) PCT No.: PCT/FR2015/053123
§ 371 (c)(1),
(2) Date: Oct. 2, 2017

(87) PCT Pub. No.: WO2016/079431
PCT Pub. Date: May 26, 2016

(65) Prior Publication Data
US 2018/0163157 A1 Jun. 14, 2018

(30) Foreign Application Priority Data
Nov. 19, 2014 (FR) ..................... 14 61213

(51) Int. Cl.
*C11B 9/00* (2006.01)
*C07C 61/04* (2006.01)
(52) U.S. Cl.
CPC .............. *C11B 9/003* (2013.01); *C07C 61/04* (2013.01); *C07B 2200/07* (2013.01); *C07C 2601/02* (2017.05)
(58) Field of Classification Search
CPC . C07B 2200/07; C07C 2601/02; C07C 61/04; C11B 9/003
See application file for complete search history.

(56) References Cited

U.S. PATENT DOCUMENTS 3,059,020 A * 10/1962 Kaiser .................. C07D 207/16
560/115
4,202,902 A * 5/1980 Carr .................... A61K 31/19
514/519
4,762,949 A 8/1988 Rinehart, Jr. et al.
2006/0128603 A1 6/2006 Widder et al.
2011/0263725 A1 10/2011 Bachmann

FOREIGN PATENT DOCUMENTS

CN 102631297 A * 8/2012
SU 406543 A * 4/1974

OTHER PUBLICATIONS

National Center for Biotechnology Information. PubChem Substance Database; SID=110603643, https://pubchem.ncbi.nlm.nih.gov/substance/110603643 (Year: 2011).*
National Center for Biotechnology Information. PubChem Substance Database; SID=110603631, https://pubchem.ncbi.nlm.nih.gov/substance/110603631; (Year: 2011).*
National Center for Biotechnology Information. PubChem Substance Database; SID=110603637, https://pubchem.ncbi.nlm.nih.gov/substance/110603637 (Year: 2011).*
National Center for Biotechnology Information. PubChem Substance Database; SID=110603625, https://pubchem.ncbi.nlm.nih.gov/substance/110603625 (Year: 2011).*
National Center for Biotechnology Information. PubChem Compound Database; CID=1713012, https://pubchem.ncbi.nlm.nih.gov/compound/1713012 (Year: 2005).*
National Center for Biotechnology Information. PubChem Compound Database; CID=1713018, https://pubchem.ncbi.nlm.nih.gov/compound/1713018 (Year: 2006).*
National Center for Biotechnology Information. PubChem Compound Database; CID=1713014, https://pubchem.ncbi.nlm.nih.gov/compound/1713014 (Year: 2005).*
National Center for Biotechnology Information. PubChem Compound Database; CID=1713018, https://pubchem.ncbi.nlm.nih.gov/compound/1713018 (Year: 2005).*
Machine Translation of Yin CN-102631297 A (Year: 2012).*
English Abstract Translation of SU-406543 A.*
Cerutti-Delasalle et al., "The (+)-cis- and (+)-trans-olibanic acids: key odorants of frankincense," Angew. Chem. Int. Ed. 55:13719-13723 (2016).
Cerutti-Delasalle et al., "The (+)-cis- and (+)-trans-olibanic acids: key odorants of frankincense," Angew. Chem. Int. Ed.(supporting information for Cerutti-Delasalle et al. publication in Angew. Chem. Int. Ed. 2016), found under http://dx.doi.org/10.1002/anie.201605242) (2016).
Frank et al., Frankincense oil derived from Boswellia carteri induces tumor cell specific cytotoxicity, BMC Complementary and Alternative Medicine, pp. 1-11 (2009).

(Continued)

*Primary Examiner* — Kara R Mcmillian
(74) *Attorney, Agent, or Firm* — Browdy and Neimark, PLLC (57) ABSTRACT

The invention relates to 2-octylcyclopropyl-1-carboxylic acid, in particular in the form of one of the isomers thereof in isolated form or in the form of a mixture of at least two of said isomers. The invention further relates to a method for synthesizing 2-octylcyclopropyl-1-carboxylic acid or at least one of the isomers thereof. Finally, the invention relates to the use of 2-octylcyclopropyl-1-carboxylic acid or of one of said isomers in isolated form or of one of the mixtures of at least two of the isomers thereof, as a perfuming agent. The invention further relates to the compositions including 2-octylcyclopropyl-1-carboxylic acid or one of said isomers in isolated form or one of the mixtures of at least two of the isomers thereof, as a perfuming agent.

16 Claims, 3 Drawing Sheets

(56) References Cited

OTHER PUBLICATIONS

Frankincense—A Cropwatch Bibliography, downloaded from www.cropwatch.org, pp. 1-43 (2011).
Ronald Bentley, The Nose as a Stereochemist. Enantiomers and Odor, Chem. Rev., 106(9):4099-4112 (p. 4099 only) (2006).
HOFMANN et al., On the Structure of Lactobacillic Acid, Journal of the American Chemical Society, 76:1799-1804 (1954).
RN 75097-00-6, "Stn-Register" cited in the first and in the second office actions in China (dated Oct. 9, 2019 and Aug. 25, 2020 respectively).

* cited by examiner

2-OCTYLCYCLOPROPYL-1-CARBOXYLIC ACID AND THE ISOMERS THEREOF, AND USES OF SAME

The invention relates to the field of perfumery and of chemical compounds that constitute the odor of frankincense.

Frankincense, also referred to as olibanum, is an aromatic resin produced from the resin of trees of the genus *Boswellia*. This oleoresin contains sugars, alcohols and acids.

Only the male tree produces the precious resin, but one has to wait a good ten years before the tree produces a quality product.

In actual perfumery, frankincense is used in the form of an essential oil or absolute. It is an essence that has a fine and complex odor and is used for its woodsy, resinous, balsamic, fresh, somewhat mineral odor, with slightly spicy aspects.

Numerous perfumes on the market contain the essential oil of olibanum as a key olfactory ingredient.

Today, the only synthetic fragrant material that has this typical note of frankincense is Mystikal® from the company Givaudan.

Thus, there is a need for synthetic molecules capable of evoking frankincense.

The studies that have been conducted by the applicant on different extracts, fractions and derivatives of olibanum have made it possible to identify several of the main components with olfactory impact.

Among these molecules with impact, the cyclopropanecarboxylic acids occupy a particular place, notably the 2-octylcyclopropyl-1-carboxylic acids of general formula (I):

Formula I which can be in the form of 4 isomers of formula II, III, IV or V.

Formula II

(1R, 2S)-2-Octylcyclopropyl-1-carboxylic acid

Formula III

(1S, 2R)-2-Octylcyclopropyl-1-carboxylic acid

Formula IV (1R, 2R)-2-Octylcyclopropyl-1-carboxylic acid

Formula V (1S, 2S)-2-Octylcyclopropyl-1-carboxylic acid

In fact, the analytical studies carried out by the applicant showed that these substances participated in a crucial manner in the base note of the essence of olibanum, which is characteristic of the "old church" odor.

Thus, the invention first relates to 2-octylcyclopropyl-1-carboxylic acids of general formula I, in the form of cis isomers of formula II or III ((1R,2S)-2-octylcyclopropyl-1-carboxylic acid and (1S,2R)-2-octylcyclopropyl-1-carboxylic acid) or trans isomers of formula IV or V ((1R,2R)-2-octylcyclopropyl-1-carboxylic acid and (1S,2S)-2-octylcyclopropyl-1-carboxylic acid) in isolated form or of a mixture in any proportions of the cis isomers of formula II or III and/or trans isomers of formulas IV and V.

Thus, it is understood that the invention relates also to the mixtures in any proportions
Isomers of formulas II, III, IV and V,
Isomers of formulas II, III and IV,
Isomers of formulas II, III and V,
Isomers of formulas II, IV and V,
Isomers of formulas III, IV and V,
Isomers of formulas II and III,
Isomers of formulas II and IV
Isomers of formulas II and V,
Isomers of formulas III and IV,
Isomers of formulas III and V,
Isomers of formulas IV and V.
as well as the isomers of formula II or III or IV or V in isolated form, that is to say pure.

The term "in any proportion" is understood to mean that each of the compounds of formula II or III or IV or V can be in the mixture in a proportion between 0.00000001% to 99.99999999%, the total quantity of the compounds in said mixtures possibly representing up to 100% of said mixture. To simplify the present text and make it clearer, the holder will not enumerate all the possible combinations, but it is clearly understood that the present application applies to all these combinations.

The term "in isolated form" is understood to mean that said compound has undergone at least one purification step and that said compound is alone, without any trace of the other compounds. For example, a compound of formula II in isolated form is a compound of formula II that has been subjected to at least one purification step and that is present alone, without trace of the compounds of formula III, IV or V, that is to say the compound is considered to be 100%.

The invention also relates to a composition including at least one 2-octylcyclopropyl-1-carboxylic acid of general formula (I). The term "composition" is understood to mean a mixture of the compound or the compounds in any proportions according to the invention and of at least one other ingredient, which are different from compounds II, III, IV or V. Here, a composition is thus not one of the compounds in isolated pure form, but can be a mixture of one of the compounds in isolated pure form with a solvent such as water, for example.

According to a first form of the invention, the composition can include 2-octylcyclopropyl-1-carboxylic acid of general formula (I) in the form of any one of the mixtures of the isomers described above, but also in the form of any one of the isomers of formula II, III, IV or V in isolated form.

According to the invention, said composition can include 2-octylcyclopropyl-1-carboxylic acid of general formula (I) in the form of any one of the mixtures of the isomers described above or in the form of any one of the isomers of formula II, III, IV or IV in isolated form, in a quantity between 0.00000001% to 99.99999999% by weight of the composition, preferably between 0.00000005% and 50% by weight of the composition, and even more preferably between 0.0000001% and 10%.

According to the invention said composition can be a cosmetic, pharmaceutical, veterinary, phytosanitary, hygienic, cleaning or washing composition.

The invention further relates to a method for synthesizing 2-octylcyclopropyl-1-carboxylic acid of general formula (I).

The invention further relates to the use of 2-octylcyclopropyl-1-carboxylic acid of general formula (I) as a perfuming agent.

According to the invention, 2-octylcyclopropyl-1-carboxylic acid of general formula (I) can be used, as a perfuming agent, in the form of any one of the mixtures of the isomers described above, but also in the form of any one of the isomers of formula II, III, IV or V in isolated form.

Advantageously, the perfuming agent can be intended to be included in any type of compositions known to the person skilled in the art, such as, for example, a perfume, an eau de parfum, an eau de toilette, hygienic products, cosmetic products, soaps, detergents, or frankincense sticks, or candles.

FIG. 2:

Other features and advantages of the invention will become apparent in the following examples, which are given for illustration and on a non-limiting basis, as well as from:

FIG. 1, which represents the reaction diagram of the synthesis of the racemic forms of the cis and trans isomers of the 2-octylcyclopropyl-1-carboxylic acid, which is described in the following examples.

FIG. 3, which represents the profiles obtained for each enantiomer of 2-octylcyclopropyl-1-carboxylic acid, which were prepared by enantioselective (Es) GC-MS with
- [(+)-9]: profile of (+)-cis-2-octylcyclopropyl-1-carboxylic acid;
- [(−)-9]: profile of (−)-cis-2-octylcyclopropyl-1-carboxylic acid;
- [(+)-8]: profile of (+)-trans-2-octylcyclopropyl-1-carboxylic acid;
- [(−)-8]: profile of (−)-trans-2-octylcyclopropyl-1-carboxylic acid.

EXAMPLE

Synthesis of the Racemic Forms of the CIS and TRANS Isomers of 2-octylcyclopropyl-1-carboxylic acid Example 1

Synthesis of ethyl (Z) and (E)-undec-2-enoate (1 and 2)

Ethoxycarbonylmethyltriphenylphosphonium bromide (53.40 g, 126.5 mmol, 1.2 eq.) is added to a solution of sodium ethylate (prepared by dissolving sodium (3.0 g, 130 mmol, 1.2 eq.) in 180 mL of absolute ethanol), and the resulting mixture is stirred for 20 min.

Nonanal (14.98 g, 105 mmol, 1 eq.) is then added, and the resulting mixture is stirred for 20 h at room temperature and then evaporated.

The residue is filtered through a silica column using petroleum ether/diethyl ether (1/1) for the elution.

After evaporation, a yellow oil is obtained, and the 2 compounds are purified by chromatography on a silica column (petroleum ether/diethyl ether (98/2)) to yield ethyl (Z)-undec-2-enoate (1) (2.66 g, 12%) and ethyl (E)-undec-2-enoate (2) (4.54 g, 27%).

Spectroscopic Analyses:

Ethyl (Z)-undec-2-enoate (1):

1H NMR (200 MHz, CDCl3):

δ=6.22 (dt, J=11.5 HZ, J=7.5 Hz, 1H), 5.77 (dt, J=11.5 Hz, J=1.7 Hz, 1H), 4.16 (q, J=7.2 Hz, 2H), 2.62 (qd, J=7.6 Hz, J=1.7 Hz, 2H), 1.20-1.50 (m, 12H), 1.29 (t, J=7.1 Hz, 3H), 0.88 (t, J=6.6 Hz, 3H) ppm.

13C NMR (50 MHz, CDCl3):

δ=166.52, 150.70, 119.67, 59.77, 31.96, 29.50, 29.42, 29.35, 29.15, 29.08, 22.76, 14.33, 14.16 ppm.

MS (E1, 70 eV):

212 (M+, 5), 167 (39), 127 (95), 115 (27), 101 (24), 99 (100), 88 (27), 81 (34), 55 (43), 43 (33), 41 (37).

Ethyl (E)-undec-2-enoate (2):

1H NMR (200 MHz, CDCl3):

δ=6.92 (dt, J=15.6 Hz, J=7.0 Hz, 1H), 5.77 (dt, J=15.6 Hz, J=1.5 Hz, 1H), 4.13 (q, J=7.2 Hz, 2H), 2.15 (qd, J=7.3 Hz, J=1.1 Hz, 2H), 1.15-1.50 (m, 12H), 1.29 (t, J=7.1 Hz, 3H), 0.88 (t, J=6.6 Hz, 3H) ppm.

13C NMR (50 MHz, CDCl3):

δ=166.73, 149.42, 121.28, 60.08, 32.24, 31.90, 29.41, 29.25, 29.21, 28.08, 22.70, 14.29, 14.10 ppm.

MS (E1, 70 eV):

212 (M+, 1), 167 (93), 124 (55), 101 (100), 99 (45), 88 (44), 84 (40), 81 (45), 73 (60), 55 (74), 43 (40), 41 (48).

Example 2

Synthesis of (Z)-undec-2-en-1-ol (3)

A 1M solution of diisobutylaluminum (DIBALH: 33 mL, 33 mmol, 2.8 eq.) in cyclohexane at −65° C. is added dropwise to a solution of ethyl (Z)-undec-2-enoate (1) (2.48 g, 11.7 mmol, 1 eq.) in toluene (70 mL). The reaction mixture is allowed to slowly return to room temperature and stirred for 13 h.

Then the reaction mixture is cooled again to −65° C., a 50% acetic acid solution (6.5 mL) is added dropwise to it, and then it is allowed to slowly return to room temperature under stirring 25 g of anhydrous sodium sulfate are then added, and the mixture is stirred for 1 h and then filtered through Celite.

The filtrates are evaporated to yield a yellow oil (2.03 g), which is then purified by chromatography on a silica column (petroleum ether/diethyl ether (95/5→9/1)) to yield (Z)-undec-2-en-1-ol (3) (1.58 g, 79%).

Spectroscopic Analyses:

1H NMR (200 MHz, CDCl3):

δ=5.55 (m, 2H), 4.17 (d, J=5.4 Hz, 2H), 2.05 (q, J=6.1 Hz, 2H), 1.20-1.45 (m, 12H), 0.88 (t, J=6.7 Hz, 3H) ppm.

13C NMR (50 MHz, CDCl3):

δ=133.27, 128.43, 58.65, 31.99, 29.73, 29.57, 29.39, 29.35, 27.54, 22.78, 14.21 ppm.

MS (EI, 70 eV):
170 (M+, <1), 95 (28), 82 (43), 81 (31), 69 (27), 68 (33), 67 (34), 57 (100), 55 (41), 43 (43), 41 (50).

Example 3

Synthesis of (E)-undec-2-en-1-ol (4)

The same method as the one applied for the synthesis of (Z)-undec-2-en-1-ol (3) (Example 2) is applied to ethyl (E)-undec-2-enoate (2) in order to lead to (E)-undec-2-en-1-ol (4) (85%).

Spectroscopic Analyses:
1H NMR (200 MHz, CDCl3):
δ=5.48-5.74 (m, 2H), 4.02 (d, J=4.6 Hz, 2H), 2.41 (br, s, 1H), 2.00 (q, J=6.9 Hz, 2H), 1.15-1.40 (m, 12H), 0.85 (t, J=6.2 Hz, 3H) ppm.
13C NMR (50 MHz, CDCl3):
δ=133.32, 128.92, 63.60, 32.30, 31.96, 29.55, 29.36, 29.29, 29.24, 22.73, 14.14 ppm.
MS (EI, 70 eV):
170 (M+, <1), 82 (43), 81 (34), 69 (32), 68 (36), 67 (41), 57 (100), 55 (51), 54 (33), 43 (49), 41 (63).

Example 4

Synthesis of trans-2-octylcyclopropyl-1-methanol (5)

A solution of diethyl zinc (10 mL, 10 mmol, 5.1 eq.) in hexane at −50° C. is added dropwise to a solution of (E)-undec-2-en-1-ol (4) (332 mg, 1.95 mmol, 1 eq.) in hexane (10 mL), and then diiodomethane (5.28 g, 19.7 mmol, 10 eq.) is added.

The reaction mixture is allowed to slowly return to room temperature and stirred for 18 h. Then, the reaction mixture is cooled again to −40° C., a solution of ammonium chloride (20 mL) is added dropwise to it, and then it is allowed to return slowly to room temperature.

The mixture is then decanted, and the aqueous phases are extracted again with 2×25 mL of diethyl ether.

The organic phases are combined, washed with brine, then dried over magnesium sulfate and evaporated to yield an orange oil (788 mg), which is then purified by chromatography on a silica column (petroleum ether/diethyl ether (98/2→8/2)) to yield trans-2-octylcyclopropyl-1-methanol (5) (275 mg, 77%).

Spectroscopic Analyses:
1H NMR (200 MHz, CDCl3):
δ=3.28-3.48 (m, 2H), 2.27 (br, s, 1H), 1.10-1.40 (m, 14H), 0.88 (t, J=6.3 Hz, 3H), 0.70-0.85 (m, 1H), 0.45-0.63 (m, 1H), 0.18-0.38 (m, 2H) ppm.
13C NMR (50 MHz, CDCl3):
δ=67.06, 33.71, 31.98, 29.71, 29.67, 29.54, 29.41, 22.74, 21.14, 17.20, 14.15, 9.99 ppm.
MS (EI, 70 eV):
143 (34), 83 (67), 82 (38), 81 (41), 69 (100), 68 (34), 67 (46), 57 (66), 55 (70), 43 (49), 41 (64).

Example 5

Synthesis of cis-2-octylcyclopropyl-1-methanol (6)

The same method as the one applied for the synthesis of trans-2-octylcyclopropyl-1-methanol (5) is applied to (Z)-undec-2-en-1-ol (3) in order to lead to cis-2-octylcyclopropyl-1-methanol (6) (64%).

Spectroscopic Analyses:
1H NMR (200 MHz, CDCl3):
δ=3.47-3.74 (m, 2H), 1.00-1.48 (m, 16H). 0.87 (t, J=6.3 Hz, 3H), 0.62-0.78 (m, 1H), −0.10-0.01 (q, 1H) ppm.
MS (EI, 70 eV):
143 (30), 83 (66), 82 (35), 81 (39), 69 (100), 68 (30), 67 (44), 57 (56), 55 (65), 43 (45), 41 (59).

Example 6

Synthesis of the mixture of the trans-2-octylcyclopropyl-1-carboxylic acids [(1S,2R)-2-octylcyclopropyl-1-carboxylic acid (III)+(1R,2R)-2-octylcyclopropyl-1-carboxylic acid (IV)]

A solution of chromium trioxide (322 mg, 3.22 mmol, 4.6 eq.) in sulfuric acid at 36%, at 0° C., is added dropwise to a solution of trans-2-octylcyclopropyl-1-methanol (5) (130 mg, 0.71 mmol, 1 eq.) in acetone (3 mL).

The reaction mixture is stirred for 1 h, then water (5 mL) is added, and the mixture is evaporated, 25 mL of additional water are added, then an extraction is carried out with 2×125 mL of dichloromethane.

The organic phases are combined, washed with brine, then dried over magnesium sulfate and evaporated to yield an oil which is then purified by chromatography on a silica column [petroleum ether/diethyl ether (9.1→8/2)] to yield the mixture of (1S,2R)-2-octylcyclopropyl-1-carboxylic acid (III) and of (1R,2R)-2-octylcyclopropyl-1-carboxylic acid (IV) (141 mg, 73%).

Spectroscopic Analyses:
1H NMR (200 MHz, CDCl3):
δ=11.73 (br, s, 1H), 1.14-1.48 (m, 17H), 0.88 (t, J=6.3 Hz, 3H), 0.70-0.82 (m, 1H) ppm.
13C NMR (50 MHz, CDCl3):
δ=181.54, 33.18, 32.02, 29.67, 29.42, 29.41, 29.19, 24.19, 22.81, 20.27, 16.52, 14.23 ppm.
MS (EI, 70 eV):
180 (1), 151 (5), 138 (15), 97 (39), 84 (34), 83 (39), 73 (100), 70 (35), 69 (51), 56 (46), 55 (79), 43 (66), 41 (72).

Example 7

Synthesis of the mixture of the cis-2-octylcyclopropyl-1-carboxylic acids [(1R,2S)-2-octylcyclopropyl-1-carboxylic acid (II) and (1S,2R)-2-octylcyclopropyl-1-carboxylic acid (III)]

The same method as the one applied for the synthesis of the mixture of the trans-2-octylcyclopropyl-1-carboxylic acids [(1S,2R)-2-octylcyclopropyl-1-carboxylic acid (III)+(1R,2R)-2-octylcyclopropyl-1-carboxylic acid (IV)] (Example 6) is applied to cis-2-octylcyclopropyl-1-methanol (6) in order to lead to the mixture of the cis-2-octylcyclopropyl-1-carboxylic acids [(1R,2S)-2-octylcyclopropyl-1-carboxylic acid (II) and (1S,2R)-2-octylcyclopropyl-1-carboxylic acid (III)] (27%).

Spectroscopic Analyses:
1H NMR (200 MHz, CDCl3):
δ=10.16 (br, s, 1H), 1.45-1.75 (m, 3H), 1.18-1.44 (m, 13H), 0.91-1.14 (m, 2H), 0.88 (t, J=6.3 Hz, 3H) ppm.
13C NMR (50 MHz, CDCl3):
δ=180.57, 32.67, 30.32 (×2), 30.09 (×2), 27.67, 23.93, 23.47, 18.85, 15.20, 14.90.

MS (E1, 70 eV):

180 (2), 151 (5), 138 (17), 97 (40), 96 (30), 84 (34), 83 (39), 73 (100), 70 (33), 69 (43), 56 (37), 55 (64), 43 (47), 41 (52).

Example 8

Synthesis of each of the enantiomers of the 2-octylcyclopropyl-1-carboxylic acids 8-9

Figure 1:
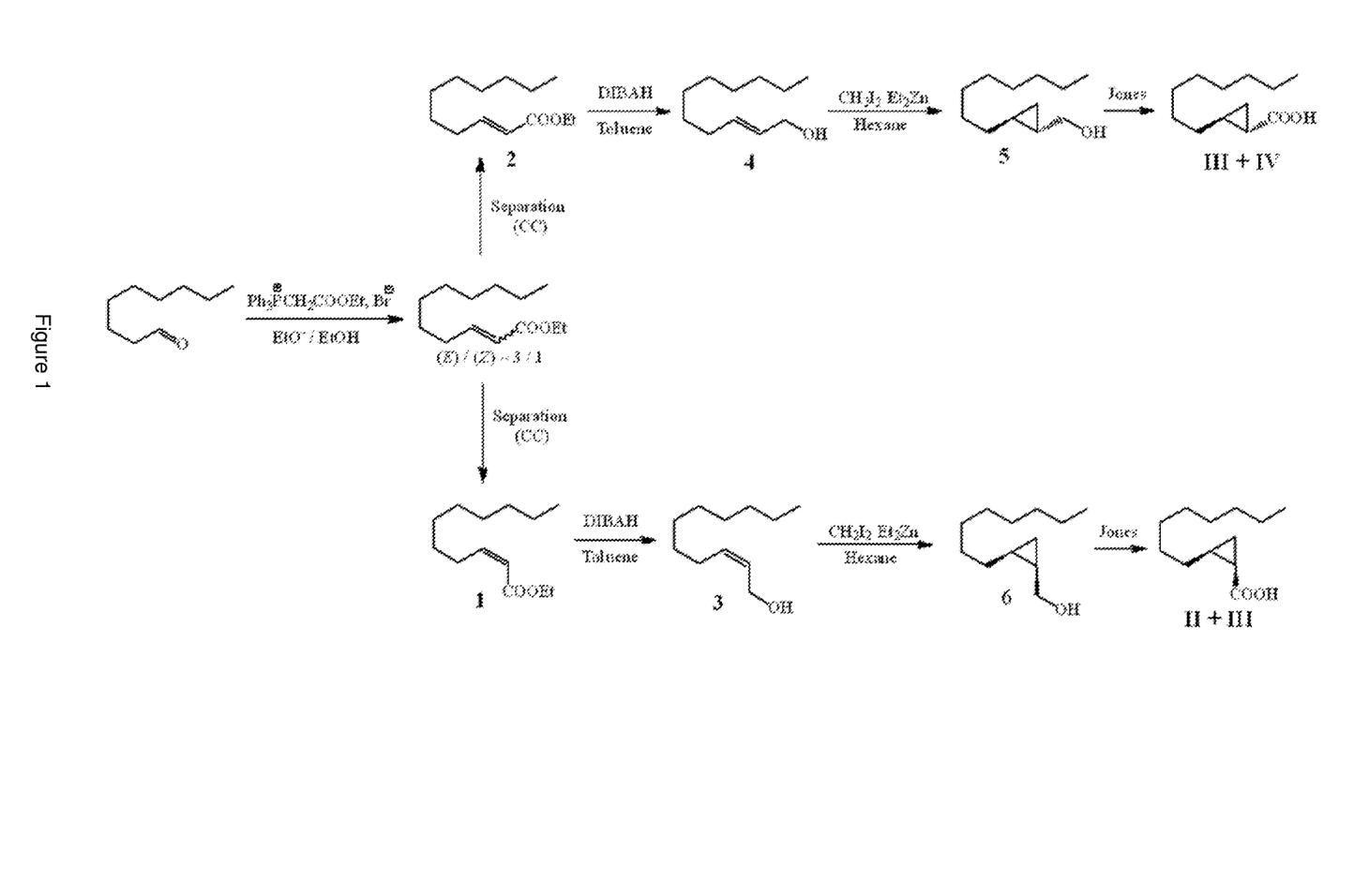
FIG. 1: reaction diagram of the synthesis of the racemic forms of the cis and trans isomers of 2-octylcyclopropyl-1-carboxylic acid.
Figure 2:
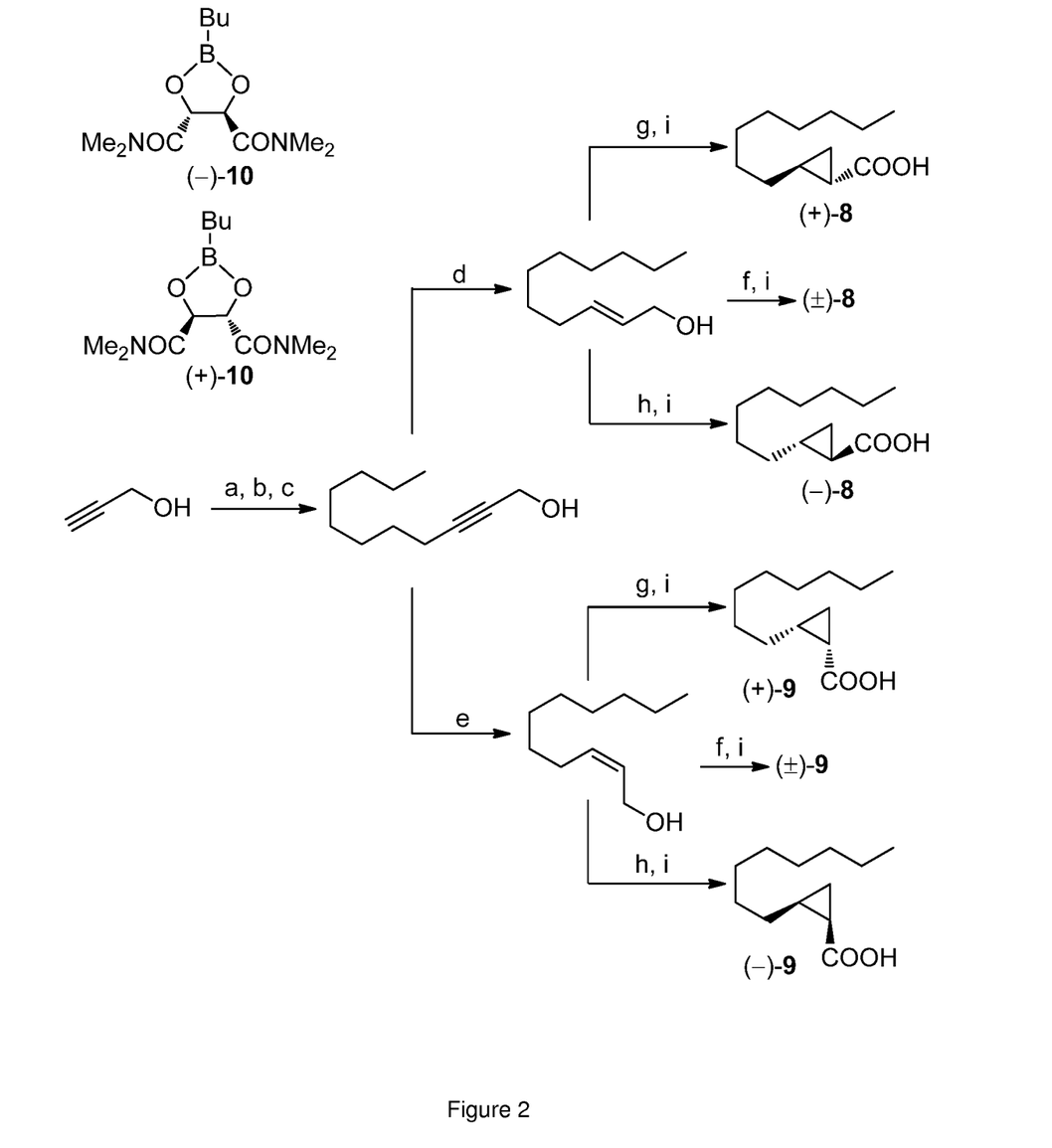
FIG. 2, which represents the reaction diagram of the synthesis of each of the enantiomers of 2-octylcyclopropyl-1-carboxylic acid [-9]
Figure 3:
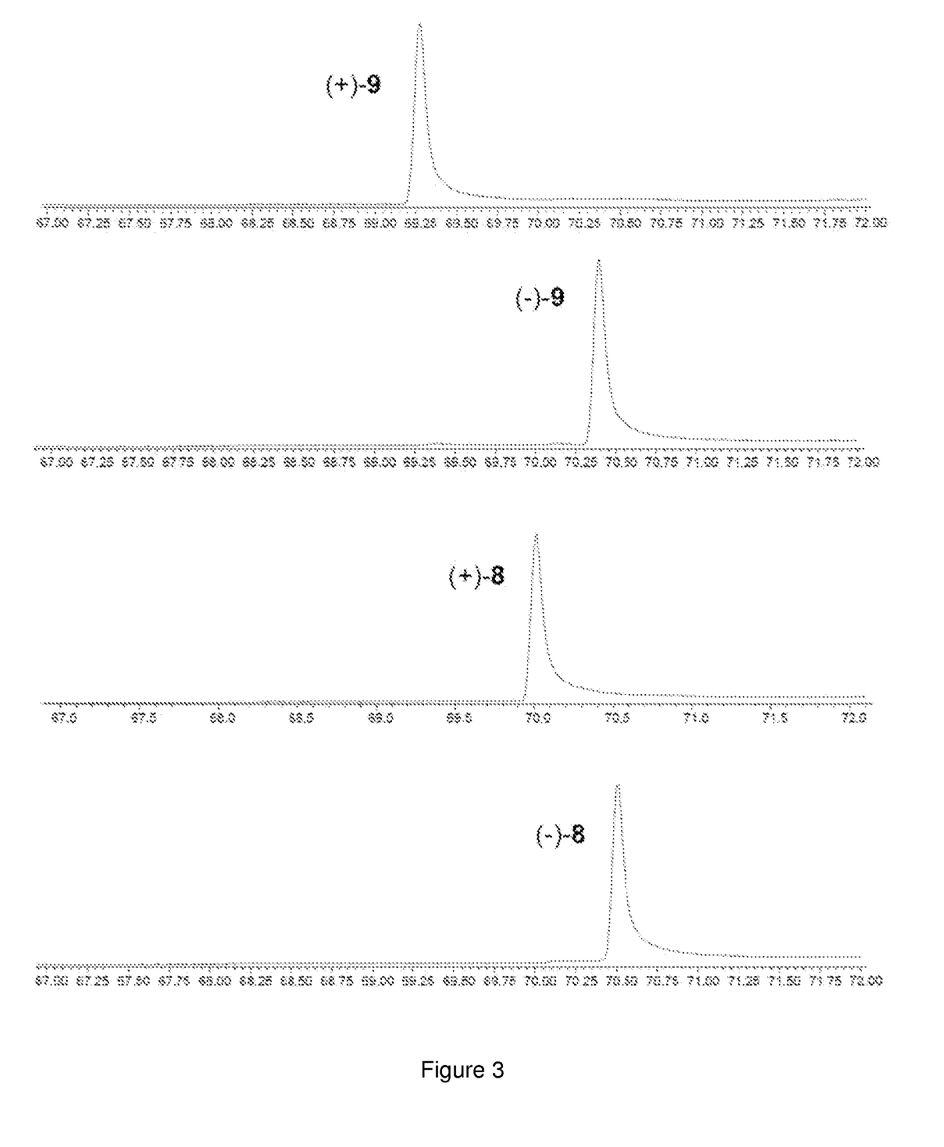
FIG. 3: Profiles of each enantiomer (8-9) of 2-octylcyclopropyl-1-carboxylic acid obtained by enantioselective (Es) GC-MS.

General Protocol:

This protocol is illustrated by FIG. 2.

Reagent and Conditions a) DHP, Amberlyst® 15, petroleum ether, room temperature, 7 h, 89% b) NaH, DMSO (4 eq.), THF, room temperature, 24 h, then 1-bromooctane, room temperature, 24 h, 67%;

c) Amberlyst® 15, methanol, 45° C., 15 h, 95%;

d) LiAlH$_4$, THF, reflux 2 h, 68%;

e) H$_2$, Ni—P2, ethylenediamine, methanol, room temperature, 60 h, 64%;

f) Et$_2$Zn, CH$_2$I$_2$, hexane, −35° C.→room temperature, 13 h;

g) (−)-10, CH$_2$Cl$_2$, −15° C., then Zn(CH$_2$I)$_2$-DME, CH$_2$Cl$_2$, −15° C.→room temperature, 15 h;

h) (+)-10, CH$_2$Cl$_2$, −15° C., then Zn(CH$_2$I)$_2$-DME, CH$_2$Cl$_2$, −15° C.→room temperature, 15 h;

i) Jones reagent, acetone, room temperature, 20 h (yields after two steps: (±)-8, 53%; (+)-8, 66%; (−)-8, 79%; (±)-9, 17%; (+)-9, 66%; (−)-9, 80%.

Detailed Procedure:

Example 8.1

Synthesis of 2-propynyloxytetrahydro-2H-pyran-2-yl ether [1]

The mixture of 144 mL (139 g, 2.47 mol, 1 eq.) of propargyl alcohol (prop-2-yn-1-ol) and of 250 mL of 3,4-dihydropyrane (230 g, 2.74 mol, 1.11 eq.) in petroleum ether (1.85 L) is prepared. Then, 3.53 g of Amberlyst® 15 are added. The suspension is then stirred at room temperature for 6 hours, then it is filtered through Celite and evaporated at reduced pressure to obtain a brown oil.

After distillation, 329.7 g (89%) of 2-propynetetrahydro-2H-pyran-2-yl ether (1) in the form of a colorless oil are obtained.

Spectral Data $^1$H NMR (200 MHz, CDCl$_3$):

δ=1.48-1.85 (m, 6H), 2.40 (t, 1H), 3.48-3.58 (m, 1H), 3.77-3.82 (m, 1H), 4.24 (m, 2H), 4.80 (t, 1H).

$^{13}$C NMR (50 MHz, CDCl$_3$):

δ=19.09, 25.43, 30.30, 54.09, 62.08, 74.09, 79.88, 96.93.

MS (E1, 70 eV): 85 (100), 82 (13), 57 (27), 56 (45), 55 (36), 53 (15), 43 (12), 41 (42), 39 (51).

Example 8.2

Synthesis of the 2-undecynyltetrahydro-2H-pyran-2-yl ether [2]

A dispersion of 60% of sodium hydride (27.16 g, 679 mmol, 2.32 eq.) is washed 2 times with petroleum ether and then covered with 400 mL of anhydrous tetrahydrofuran (THF).

To this suspension, 88 g of anhydrous DMSO (80 mL, 1.12 mol, 3.85 eq.) are added under stirring, and then 41 g of 2-propynetetrahydro-2H-pyran-2-yl ether [1] (40.6 mL, 290 mmol, 1 eq.) obtained previously are added.

After 24 hours of stirring at room temperature, 141 g of 1-bromooctane (126 mL, 730 mmol, 2.5 eq.) are added dropwise over a period of approximately one hour.

The internal temperature of the reaction reaches 38° C., then decreases.

The reaction medium is stirred for 48 h at room temperature and optionally cooled in an ice bath.

200 mL of an aqueous solution saturated with sodium hydrogen carbonate are then added dropwise. Then, 200 mL of water are added.

After decanting of the biphasic mixture obtained, the aqueous phase is washed 2 times with 200 mL of petroleum ether.

The combined organic phases are washed with brine, dried over magnesium sulfate and evaporated at reduced pressure. The dark brown oil obtained is then purified by vacuum distillation (0.46 mbar) in order to obtain 49.5 g (67%) of 2-undecynyltetrahydro-2H-pyran-2-yl ether [2] in the form of a pale-yellow oil.

Spectral Data:

$^1$H NMR (200 MHz, CDCl$_3$):

δ=0.88 (t, 3H), 1.20-1.97 (M, 18H), 2.15-2.31 (m, 2H), 3.46-3.69 (m, 1H), 3.78-3.86 (m, 1H), 4.12-4.38 (m, 2H), 4.81 (1H, br t),

$^{13}$C NMR (50 MHz, CDCl$_3$):

δ=14.19, 18.92, 19.24, 22.76, 25.51, 28.72, 28.99, 29.20, 29.30, 30.41, 31.94, 54.74, 62.07, 75.81, 86.86, 96.70.

MS (E1, 70 eV): 101 (32), 95 (50), 93 (18), 85 (100), 81 (39), 79 (24), 67 (40), 55 (40), 43 (24), 41 (38).

Example 8.3

Synthesis of 2-undecynol [3]

1.030 g of 2-undecynyltetrahydro-2H-pyran-2-yl ether [2] (4.08 mmol) obtained previously are added to a suspension of 73 mg Amberlyst® H-15 in 16 mL of methanol. This mixture is stirred at 45° C. for 15 h, filtered through Celite, evaporated at reduced pressure, and filtered through a short buffer of silica gel using a 9/1 petroleum ether/diethyl ether mixture for rinsing. After evaporation of the solvents, 0.651 g of 2-undecynol (3) (95%) in the form of a slightly yellow oil are obtained.

Spectral Data:
$^1$H NMR (200 MHz, CDCl$_3$):
δ=0.88 (t, 3H), 1.22-1.61 (m, 12H), 2.15-2.26 (m, 2H), 4.20-4.29 (m, 2H), $^{13}$C NMR (50 MHz, CDCl$_3$):
δ=14.22, 18.86, 22.78, 27.73, 29.01, 29.23, 29.31, 31.96, 51.53, 78.38, 87.78.
MS (E1, 70 eV): 93 (56), 83 (45), 81 (68), 79 (63), 70 (64), 67 (78), 55 (100), 43 (52), 41 (93), 39 (48).

Example 8.4

Synthesis of (Z)-undec-2-en-1-ol [4]

2.69 g (10.8 mmol, 0.26 eq.) of nickel(II) acetate tetrahydrate (Ni(OAc)$_2$, 4H$_2$O) are dissolved in 66 mL of methanol by stirring under argon, and the solution obtained is then cooled in an ice bath.

457 mg of sodium borohydride (12.1 mmol, 0.29 eq.) are then added quickly all at once, and the ice bath is removed.

After 10 minutes of stirring, 1.22 g of 1,2-ethylenediamine (20.3 mmol, 0.48 eq.) are added, followed, after 10 minutes, by the addition of 7.07 g of 2-undecynol [3] (42 mmol, 1 eq.).

The atmosphere of the bottle is then purged and maintained under a slight overpressure of hydrogen by means of a tank.

The reaction mixture is then mixed for 54 h, and the reaction is monitored by GC-MS. In order to ensure the complete conversion of the starting material, two additional portions of Ni(OAc)$_2$, 4H$_2$O/sodium borohydride/1,2-ethylenediamine are added sequentially, up to a total additional quantity of 563 mg (2.26 mmol, 0.05 eq.) of Ni(OAc)$_2$, 4H$_2$O, 139 mg (3.69 mmol, 0.09 eq.) of sodium borohydride and 352 mg (5.86 mmol, 0.14 eq.) of 1,2-ethylenediamine.

The reaction medium is then filtered through Celite, and the solid is washed with dichloromethane.

The filtrate thus obtained is evaporated, and 100 mL of diethyl ether and 100 mL of water are added to this residue.

After decanting, the dark blue aqueous phase is washed with diethyl ether (3×50 mL), and the combined organic phases are then washed with brine, dried over magnesium sulfate and evaporated at reduced pressure. The green oil is then purified by chromatography on a silica gel column (petroleum ether/diethyl ether (95/5→9/1)) until 4.32 g (60%) (Z)-undec-2-en-1-ol [4] are obtained in the form of a colorless oil.

Spectral Data:
$^1$H NMR (200 MHz, CDCl$_3$):
δ=5.55 (m, 2H), 4.17 (d, 2H), 2.05 (q, 2H), 1.20-1.45 (m, 12H), 0.88 (t, 3H) ppm.
$^{13}$C NMR (50 MHz, CDCl$_3$):
δ=133.27, 128.43, 58.65, 31.99, 29.73, 29.57, 29.39, 29.35, 27.54, 22.78, 14.21 ppm.
MS (E1, 70 eV): 170 (M$^+$<1), 95 (28), 82 (43), 81 (31), 69 (27), 68 (33), 67 (34), 57 (100), 55 (41), 43 (43), 41 (50).
IR (neat) ν$_{max}$ 3315, 2923, 2854, 1464, 1033 cm$^{-1}$.

Example 8.5

Synthesis of (E)-undec-2-en-1-ol [SI-5]

6.9 g of SI-3 (41 mmol, 1.00 eq.) are added to 3.53 g of a suspension of lithium tetrahydruroaluminate (LiAlH$_4$) (93 mmol, 2.27 eq.) in anhydrous THF (650 mL), and the mixture is heated at reflux for 2 h 30.

After cooling in an ice bath, the reaction mixture is then quenched by careful addition of a saturated solution of sodium sulfate (12 mL), followed by the addition of 14 g of anhydrous sodium sulfate. The mixture is then stirred for 2 h, the resulting gray suspension is then filtered through Celite, and the solid is washed exhaustively with diethyl ether. After evaporation of the solvent, the brown oil is purified by chromatography on a silica gel column (petroleum ether/diethyl ether (95/5→9/1)) until 4.47 g of (E)-undec-2-en-1-ol [SI-5] (64%) are obtained in the form of a colorless oil.

Spectral Data:
$^1$H NMR (200 MHz, CDCl$_3$):
δ=5.48-5.74 (m, 2H), 4.02 (d, J=4.6 Hz, 2H), 2.41 (br, s, 1H), 2.00 (q, J=6.9 Hz, 2H), 1.15-1.40 (m, 12H), 0.85 (t, J=6.2 Hz, 3H) ppm.
$^{13}$C NMR (50 MHz, CDCl$_3$):
δ=133.32, 128.92, 63.60, 32.30, 31.96, 29.55, 29.36, 29.29, 29.24, 22.73, 14.14 ppm. MS (E1, 70 eV): 170 (M$^+$, <1), 82 (43), 81 (34), 69 (32), 68 (36), 67 (41), 57 (100), 55 (51), 54 (33), 43 (49), 41 (63).
IR (neat) ν$_{max}$ 3315, 2923, 2854, 1464, 1033 cm$^{-1}$.

Example 8.6

Synthesis of (±)-trans-2-octylcyclopropyl-1-methanol [(±)-6]

To a solution of 332 mg of (E)-undec-2-en-1-ol (5) (1.95 mmol, 1 eq.) in 10 mL of hexane, 10 mL of a 1M diethyl zinc solution (10 mmol, 5.1 eq.) in hexane at −50° C. are added dropwise, followed by 5.28 g of diiodomethane (19.7 mmol, 10 eq.).

The reaction mixture is heated slowly to room temperature and stirred for 18 h, then it is cooled again to −40° C., quenched by the dropwise addition of a saturated ammonium chloride solution (20 mL). The mixture is then allowed to heat to room temperature under stirring. The mixture is then decanted, and the aqueous phase is washed with 2×25 mL of diethyl ether. The combined organic phases are washed with brine, dried over magnesium sulfate and evaporated at reduced pressure to obtain an orange oil (788 mg), which is then purified by chromatography on a silica gel column (petroleum ether/diethyl ether (98/2→8/2)) until 275 mg of (±)-trans-2-octylcyclopropyl-1-methanol [(±)-6] (77%) are obtained in the form of a colorless oil.

Spectral Data:

$^1$H NMR (200 MHz, CDCl$_3$):

δ=3.28-3.48 (m, 2H), 2.27 (br, s, 1H), 1.10-1.40 (m, 14H), 0.88 (t, 3H), 0.70-0.85 (m, 1H), 0.45-0.63 (m, 1H), 0.18-0.38 (m, 2H) ppm.

$^{13}$C NMR (50 MHz, CDCl$_3$): δ=67.06, 33.71, 31.98, 29.71, 29.67, 29.54, 29.41, 22.74, 21.14, 17.20, 14.15, 9.99 ppm.

MS (EI, 70 eV): 143 (34), 83 (67), 82 (38), 81 (41), 69 (100), 68 (34), 67 (46), 57 (66), 55 (70), 43 (49), 41 (64).

IR (neat) v$_{max}$ 3300, 2922, 2852, 1464, 1032 cm$^{-1}$

Example 8.9

Synthesis of (±)-trans-2-octylcyclopropyl-1-carboxylic acid [(±)-8]

To a solution of 130 mg of (±)-trans-2-octylcyclopropyl-1-methanol [(±)-6] (0.71 mmol, 1 eq.) in 3 mL of acetone, a solution of 322 mg of chromium trioxide (3.22 mmol, 4.6 eq.) in 1.08 mL of 36% sulfuric acid at 0° C. is added dropwise. The reaction mixture is heated slowly to room temperature and stirred for 1 h.

5 mL of water are then added, and the mixture is evaporated, 25 mL of water are added to mixture, and the mixture is washed with 2×125 mL of dichloromethane. The combined organic phases are then washed with brine, dried over magnesium sulfate and evaporated at reduced pressure until the obtaining of residue, which is then purified by chromatography on a silica gel column (petroleum ether/diethyl ether (9.1→8/2)) in order to obtain 103 mg of (±)-trans-2-octylcyclopropyl-1-carboxylic acid [(±)-8] (73%).

Spectral Data:

$^1$H NMR (200 MHz, CDCl$_3$):

δ=11.73 (br, s, 1H), 1.14-1.48 (m, 17H), 0.88 (t, 3H), 0.70-0.82 (m, 1H) ppm, $^{13}$C NMR (50 MHz, CDCl$_3$):

δ=181.54, 33.18, 32.02, 29.67, 29.42, 29.41, 29.19, 24.19, 22.81, 20.27, 16.52, 14.23 ppm.

MS (EI, 70 eV): 180 (1), 151 (5), 138 (15), 97 (39), 84 (34), 83 (39), 73 (100), 70 (35), 69 (51), 56 (46), 55 (79), 43 (66), 41 (72).

IR (neat) v$_{max}$ 2917, 2850, 1687, 1456, 1431, 1222, 874 cm$^{-1}$

Example 8.10

Synthesis (±)-cis-2-octylcyclopropyl-1-methanol [7]

The same procedure as above applied to (Z)-undec-2-en-1-ol [4] leads to obtaining (±)-cis-2-octylcyclopropyl-1-methanol [7] (64%) in the form of a colorless oil.

Spectral Data:

$^1$H NMR (200 MHz, CDCl$_3$): δ=3.47-3.74 (m, 2H), 1.00-1.48 (m, 16H), 0.87 (t, 3H), 0.62-0.78 (m, 1H), −0.10-0.01 (q, 1H) ppm.

MS (EI, 70 eV): 143 (30), 83 (66), 82 (35), 81 (39), 69 (100), 68 (30), 67 (44), 57 (56), 55 (65), 43 (45), 41 (59).

Example 8.11

Synthesis of (±)-cis-2-octylcyclopropyl-1-carboxylic acid [(±)-9]

The same procedure as above applied to cis-2-octylcyclopropyl-1-methanol [(±)-7] leads to obtaining (±)-cis-2-octylcyclopropyl-1-carboxylic acid [(±)-9] (27%) in the form of a colorless oil.

Spectral Data:
$^1$H NMR (200 MHz, CDCl$_3$):
δ=10.16 (br, s, 1H), 1.45-1.75 (m, 3H), 1.18-1.44 (m, 13H), 0.91-1.14 (m, 2H), 0.88 (t, 3H) ppm.
$^{13}$C NMR (50 MHz, CDCl$_3$): δ=180.57, 32.67, 30.32 (×2), 30.09 (×2), 27.67, 23.93, 23.47, 18.85, 15.20, 14.90.
MS (E1, 70 eV): 180 (2), 151 (5), 138 (17), 97 (40), 96 (30), 84 (34), 83 (39), 73 (100), 70 (33), 69 (43), 56 (37), 55 (64), 43 (47), 41 (52).
IR (neat) $v_{max}$ 2923, 2854, 1693, 1033 cm$^{-1}$

Example 8.12

Synthesis of (1S,2S)-trans-2-octylcyclopropyl-1-methanol [(1S,2S)-6]

In a first step, a solution of bisiodozinc DME complex [Zn(CH$_2$I)$_2$.DME] is prepared by adding diiodomethane (19.2 mL, 63.8 g, 238 mmol, 21.1 eq.) within 1 h (by means of syringe pump) to a 1M diethyl zinc solution (120 mL, 120 mmol, 10.64 eq.) in a mixture of anhydrous dichloromethane (240 mL) and of dimethoxyethane (12.4 mL) at −15° C.

The resulting milky solution is kept at cold temperature in an ice bath.

Simultaneously, 1.92 g of (E)-undec-2-en-1-ol (5) (11.3 mmol, 1 eq.) and 3.60 g of (4R,5R)-2-butyl-N,N,N',N'-tetramethyl-1,3,2-dioxaborolane-4,5-dicarboxamide [(−)-10] (13.3 mmol, 1.18 eq.) are diluted in 60 mL of dichloromethane, and the mixture is cooled to −14° C.

The solution of Zn(CH$_2$I)$_2$.DME complex, which has been prepared beforehand, is then slowly introduced through a cannula into the mixture within approximately 12 min, and stirred at a temperature between −12° C. and −18° C. for 4 h, then the entire mixture is allowed to return slowly to room temperature under stirring overnight. The mixture is then quenched by the dropwise addition of a saturated ammonium chloride solution (80 mL) under stirring. The mixture is then decanted, and the aqueous phase is washed with 3×60 mL of diethyl ether. The combined organic phases are washed successively with 5M potassium hydroxide, 10% hydrochloric acid and saturated sodium bicarbonate solutions, and optionally two times with brine. Then, the mixture is dried over magnesium sulfate and evaporated at reduced pressure until a yellow oil is obtained, which is then purified by filtration through a short buffer of silica gel (20 g). The first portion of the filtrate (using 80 mL of petroleum ether) is discarded, and the product is eluted with 150 mL of petroleum ether/diethyl ether (2/1) in order to obtain, after evaporation, 2.08 g of (1S,2S)-trans-2-octylcyclopropyl-1-methanol [(1S,2S)-6] (98%) in the form of a pale-yellow oil.

The spectral data are identical to those of the [(±)-6].

Example 8.13

Synthesis of the (+)-trans-2-octylcyclopropyl-1-carboxylic acid [(+)-8]

The oxidation procedure used for the synthesis of [(±)-8] are applied to (1S,2S)-6, with a reaction time of 20 h, in order to obtain (+)-(1S,2S)-8 (67%).

The spectral data are identical to those of the [(±-8].

Example 8.14

Synthesis of (1R,2R)-trans-2-octylcyclopropyl-1-methanol [(1R,2R)-6]

(1R, 2R)-6

The asymmetric cyclopropanation procedure used for the synthesis of (1S,2S)-6 is applied to [5], with [(+)-10] used as chiral auxiliary, and leads to [(1R,2R)-6] (quant.).
The spectral data are identical to those of 6.

Example 8.15

Synthesis of (±)-trans-2-octylcyclopropyl-1-carboxylic acid [(−)-8]

The oxidation procedure used for [(±)-8] is applied to [(1R,2R)-6], with a reaction time of 20 h, and leads to [([sic])-(1R,2R)-8] (79%).
The spectral data are identical to those of [(±-8].

Example 8.16

Synthesis of (1S,2R)-cis-2-octylcyclopropyl-1-methanol [(1S,2R)-7]

The asymmetric cyclopropanation procedure used for the synthesis of [(1S,2S)-6] is applied to [4] and leads to [(1S,2R)-7] (quant.).
The spectral data are identical to those of [(±)-7].

Example 8.17

Synthesis of (+)-cis-2-octylcyclopropyl-1-carboxylic acid [(+)-9]

The oxidation procedure used for [(±)-8] is applied to [(1S,2R)-7], with a reaction time of 20 h, and leads to [(+)-(1S,2R)-9] (66%).
The spectral data are identical to those of [(±)-9].

Example 8.18

Synthesis of (1R,2S)-cis-2-octylcyclopropyl-1-methanol [(1R,2S)-7]

The asymmetric cyclopropanation procedure used for the synthesis of [(1S,2S)-6] is applied to [4] with [(+)-10] used as chiral auxiliary and leads to [(1R,2S)-7] (quant.).
The spectral data are identical to those [(±)-7].

Example 8.19

Synthesis of (−)-cis-2-octylcyclopropyl-1-carboxylic acid [(−)-9]

(1R, 2S)-7

(−)-9

The oxidation procedure used for [(±)-8] is applied to [(1R,2S)-7], with a reaction time of 20 h, and leads to [(−)-(1R,2S)-9] (80%).

The spectral data are identical to those of [(±)-9].

The invention claimed is:

1. A composition comprising a mixture of isomers of 2-octylcyclopropyl-1-carboxylic acid, each of said isomers being identified as:

(−)-cis-2-octylcyclopropyl-1-carboxylic acid, designated as compound (−)-9, of formula II Formula II

(+)-cis-2-octylcyclopropyl-1-carboxylic acid, designated as compound (+)-9, of formula III Formula III (−)-trans-2-octylcyclopropyl-1-carboxylic acid, designated as compound (−)-8, of formula IV

Formula IV and (+)-trans-2-octylcyclopropyl-1-carboxylic acid, designated as compound (+)-8, of formula V Formula V said mixture of isomers consisting of isomers selected from the group consisting of:

the (−)-9, (+)-9 and (−)-8 isomers of formulas II, III and IV,
the (−)-9, (+)-9 and (+)-8 isomers of formulas II, III and V,
the (−)-9, (−)-8 and (+)-8 isomers of formulas II, IV and V,
the (+)-9, (−)-8 and (+)-8 isomers of formulas III, IV and V,
the (−)-9 and (−)-8 isomers of formulas II and IV,
the (−)-9 and (+)-8 isomers of formulas II and V, and
the (+)-9 and (−)-8 isomers of formulas III and IV.

2. The composition according to claim 1, further including at least one other ingredient suitable for formulating a cosmetic, pharmaceutical, veterinary, phytosanitary, hygienic, cleaning, or washing composition.

3. A scented product comprising a perfuming agent and at least one additional agent suitable for formulating a scented product, wherein said perfuming agent is a composition in accordance with claim 1.

4. The scented product in accordance with claim 3, wherein said product is a detergent, a frankincense stick, or a candle.

5. The scented product in accordance with claim 3, wherein said product is a perfume, an eau de parfum, an eau de toilette, a hygienic product, a cosmetic product, or a soap.

6. A method of using a scented product in accordance with claim 5 comprising applying the scented product to the skin.

7. A composition comprising a single isomer of 2-octylcyclopropyl-1-carboxylic acid, wherein the single isomer of 2-octylcyclopropyl-1-carboxylic acid present in the composition is identified as:

(−)-cis-2-octylcyclopropyl-1-carboxylic acid, designated as compound (−)-9, of formula II

Formula II or (−)-trans-2-octylcyclopropyl-1-carboxylic acid, designated as compound (−)-8, of formula IV Formula IV and further including at least one other ingredient suitable for formulating a cosmetic, pharmaceutical, veterinary, phytosanitary, hygienic, cleaning, or washing composition or a scented product.

8. A scented product containing a perfuming agent, comprising a composition according to claim 7, wherein said perfuming agent is said compound (−)-9 or (−)-8 and wherein said at least one other ingredient is suitable for formulating a scented product.

9. A scented product containing a perfuming agent, in the form of a detergent, a frankincense stick, or a candle, comprising a composition according to claim 7, wherein said perfuming agent is said compound (−)-9 or (−)-8 and wherein said at least one other ingredient is an agent suitable for formulating a scented product which is a detergent, a frankincense stick or a candle.

10. A scented product containing a perfuming agent, in the form of a perfume, an eau de parfum, an eau de toilette, a hygienic product, a cosmetic product, or a soap, comprising a composition according to claim 7, wherein said perfuming agent is said compound (−)-9 or (−)-8 and wherein said at least one other ingredient is suitable for formulating a scented product which is a perfume, an eau de parfum, an eau de toilette, a hygienic product, a cosmetic product, or a soap.

11. A method of using a scented product in accordance with claim 10, comprising applying the scented product to the skin.

12. A method of using a scented product comprising a mixture of isomers of 2-octylcyclopropyl-1-carboxylic acid and at least one additional agent suitable for formulating a scented product, said mixture of isomers consisting of the (−)-8 and (+)-8 isomers of formulas IV and V identified as:

(−)-trans-2-octylcyclopropyl-1-carboxylic acid, designated as compound (−)-8, of formula IV Formula IV and (+)-trans-2-octylcyclopropyl-1-carboxylic acid, designated as compound (+)-8, of formula V Formula V the method comprising applying the scented product to the skin, applying the scented product on a surface or diffusing the scented product in an environment.

13. The scented product in accordance with claim 9 in the form of a frankincense stick or a candle.

14. The scented product in accordance with claim 4 in the form of a frankincense stick or a candle.

15. A method of using a scented product comprising a mixture of isomers of 2-octylcyclopropyl-1-carboxylic acid and at least one additional agent suitable for formulating a scented product, said mixture of isomers consisting of the (−)-9, (+)-9, (−)-8 and (+)-8 isomers of formulas II, III, IV and V identified as:

(−)-cis-2-octylcyclopropyl-1-carboxylic acid, designated as compound (−)-9, of formula II

Formula II (+)-cis-2-octylcyclopropyl-1-carboxylic acid, designated as compound (+)-9, of formula III Formula III

(−)-trans-2-octylcyclopropyl-1-carboxylic acid, designated as compound (−)-8, of formula IV Formula IV and (+)-trans-2-octylcyclopropyl-1-carboxylic acid, designated as compound (+)-8, of formula V

Formula V the method comprising applying the scented product on a surface other than the skin or diffusing the scented product in an environment.

16. A method of using a scented product comprising a mixture of isomers of 2-octylcyclopropyl-1-carboxylic acid and at least one additional agent suitable for formulating a scented product, said mixture of isomers consisting of the (−)-9 and (+)-9 isomers of formulas II and III identified as:

(−)-cis-2-octylcyclopropyl-1-carboxylic acid, designated as compound (−)-9, of formula II Formula II (+)-cis-2-octylcyclopropyl-1-carboxylic acid, designated as compound (+)-9, of formula III Formula III the method comprising applying the scented product to the skin, applying the scented product on a surface, or diffusing the scented product in an environment.

* * * * *

UNITED STATES PATENT AND TRADEMARK OFFICE
CERTIFICATE OF CORRECTION

PATENT NO. : 11,236,287 B2
APPLICATION NO. : 15/528225
DATED : February 1, 2022
INVENTOR(S) : Nicolas Baldovini et al.

It is certified that error appears in the above-identified patent and that said Letters Patent is hereby corrected as shown below:

On the Title Page

At item (73) Assignees, delete: "Albert Vielle, Vallauns (FR)" and insert --Albert Vieille, Vallauris (FR)--.

Signed and Sealed this
Twelfth Day of July, 2022

Katherine Kelly Vidal
*Director of the United States Patent and Trademark Office*